United States Patent [19]

Alig et al.

[11] Patent Number: 4,988,714
[45] Date of Patent: Jan. 29, 1991

[54] PYRIDINE-ETHANOLAMINE DERIVATIVES

[75] Inventors: Leo Alig, Kaiseraugst; Marcel Müller, Frenkendorf, both of Switzerland

[73] Assignee: Hoffmann-La Roche Inc., Nutley, N.J.

[21] Appl. No.: 236,802

[22] Filed: Aug. 26, 1988

Related U.S. Application Data

[62] Division of Ser. No. 57,150, Jun. 3, 1987, Pat. No. 4,800,206.

[30] Foreign Application Priority Data

Jun. 27, 1986 [CH] Switzerland ............... 2608/86
Mar. 27, 1987 [CH] Switzerland ............... 1186/87

[51] Int. Cl.⁵ ................... A61K 31/44; C07D 213/30
[52] U.S. Cl. ................... 514/357; 546/334; 546/335; 546/337
[58] Field of Search ............ 546/334, 335, 337; 514/357

[56] References Cited

U.S. PATENT DOCUMENTS 4,358,455 11/1982 Atkinson et al. ............ 546/312
4,460,580 7/1984 Ostermayer et al. ......... 514/357
4,692,465 9/1987 Hindley et al. ............. 514/539

FOREIGN PATENT DOCUMENTS 5848 12/1979 European Pat. Off.
70133 1/1983 European Pat. Off.
99707 2/1984 European Pat. Off.
236624 11/1985 European Pat. Off.
164700 12/1985 European Pat. Off.

OTHER PUBLICATIONS

Zymalkowski, F. et al., Syntheses of Pyridine Derivatives with Potential Circulatory System Action, Arch. Pharm. 294, 453-68 (1961) CA 56:2415e.
L. Polo Friz, Nitrogen-Substituted Derivatives of 1-(-4-Pyridyl)-2-amino-ethanol Farmaco (Pana) Ed. Sci. 18 (12), 972-80 (1963) CA 60:6815a.
Schultz, D. E., Synthesis of 1-(4-pyridyl)-2-amino-alkanol Dihydrochlorides, Arch. Pharm. Ber. Deut. Pharm. Ger. 1972 305 (4), 248-53 (Ger) CA 77:61749n.
Barth, W. E., 2-(hydroxymethyl)-3-hydroxy-6-(1-hydroxy-2-aminoethyl)pyridines Ger. Offen. #2,204,195. DT 2406-930 (U.S. Pat. No. 4,195,090) Derwent 61811V/35.
Chem. Ab. 95:150461c—Jpn. Kokai Tokyo Koho 81 55,369 Yoshitomi Pharmaceutical Industries, Ltd.—Pyridinemethanol Derivatives.
Yashitomi Pharmaceutical Ind. CA 95:150462c.

Primary Examiner—Jane T. Fan
Attorney, Agent, or Firm—George M. Gould; Bernard S. Leon; William G. Isgro

[57] ABSTRACT

Pyridine-ethanolamines of the formula

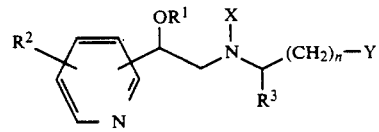

wherein n, X, Y, $R^1$, $R^2$ and $R^3$ have the significances given in the description, their corresponding enantiomers, diastereomers, and racemates as well as the physiologically compatible salts thereof are described. The compounds of formula I have catabolic activity and can be used for the treatment of obesity and of diabetes mellitus or of conditions which are associated with an increased protein breakdown, or as feed additives for fattening animals. The compounds of formula I can be prepared by alkylating the primary or secondary amines corresponding to the secondary or tertiary amines of formula I.

24 Claims, No Drawings

PYRIDINE-ETHANOLAMINE DERIVATIVES

This is a division, of application Ser. No. 057,150 filed June 3, 1987, which is now U.S. Pat. No. 4,800,206, issued Jan. 24, 1989.

BRIEF DESCRIPTION OF THE INVENTION

The invention relates to pyridineethanolamine derivatives a process for their preparation and pharmaceutical preparations based on these compounds.

The Pyridine derivatives in accordance with the invention are compounds of the formula

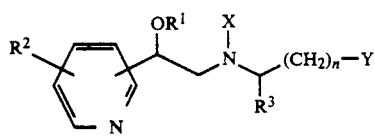

wherein
n is 1 or 2,
X is hydrogen, lower-alkyl, lower-alkoxy-lower-alkyl or a group $X^a$ of the formula

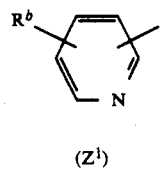

Z is a group of the formula

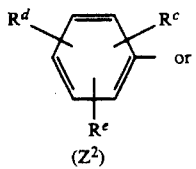 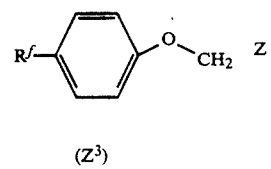

Y is a group or

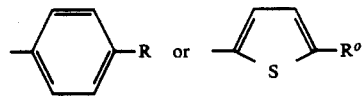

$R^o$ is lower-alkyl, $COR^4$ or $C(R^5)\!\!=\!\!CHCOR^4$
R is $R^o$ or is $OR''$.
R'' is hydrogen, lower-alkyl, lower-alkanoyl, $(CH_2)_{1-6}$—OH, $(CH_2)_{1-6}$—O$(CH_2)_{1-6}$—$R^6$ or $(CH_2)_{1-6}$—$COR^4$.
$R^1$ and $R^a$ are hydrogen, lower-alkanoyl, benzoyl or $(CH_2)_{1-6}$-OH.
$R^2$ and $R^b$ are hydrogen, Cl, Br or $CF_3$.
$R^3$ and $R^5$ are hydrogen or $CH_3$,
$R^4$ is hydroxy, lower-alkoxy or $N(R^7, R^8)$,
$R^6$ hydrogen, $R^g$, OH or $COR^4$,
$R^7$ and $R^8$ are hydrogen or lower-alkyl,
$R^c$ and $R^e$ are hydrogen, Cl, F, Br or $CF_3$,
$R^d$ is hydrogen or $NH_2$,
$R^f$ is hydrogen, $CH_3CONH$, $NH_2COCH_2$ or $R^9CH_2CH_2OCH_2CH_2O$
$R^g$ and $R^9$ are phenyl or phenyl substituted by Cl, F or Br,
as well as the physiologically compatible salts thereof.

DETAILED DESCRIPTION OF THE INVENTION

The invention relates to pyridineethanolamine derivatives, a process for their preparation and pharmaceutical preparations based on these compounds.

The pyridine derivatives in accordance with the invention are compounds of the formula

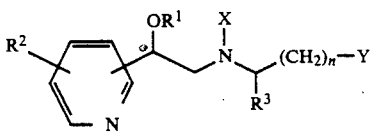

wherein
n is 1 or 2,
X is hydrogen, lower-alkyl, lower-alkoxy-lower-alkyl or a group $X^a$ of the formula

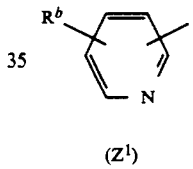

Z is a group of the formula

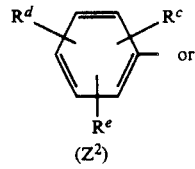 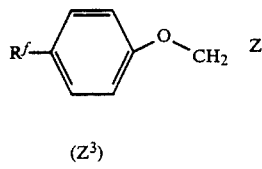

Y is a group

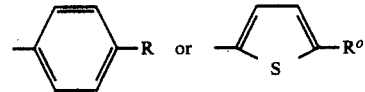

$R^o$ is lower-alkyl, $COR^4$ or $C(R^5)\!\!=\!\!CHCOR^4$
R is $R^o$ or is $OR'''$,
R'' is hydrogen lower-alkyl lower-alkanoyl, $(CH_2)_{1-6}$-OH, $(CH_2)_{1-6}$-O$(CH_2)_{1-6}$-$R^6$ or $(CH_2)_{1-6}$-$COR^4$,
$R^1$ and $R^a$ are hydrogen, lower-alkanoyl, benzoyl or $(CH_2)_{1-6}$-OH,
$R^2$ and $R^b$ are hydrogen Cl, Br or $CF_3$,
$R^3$ and $R^5$ are hydrogen or $CH_3$,
$R^4$ is hydroxy, lower-alkoxy or $N(R^7, R^8)$,
$R^6$ is hydrogen, $R^g$, OH or $COR^4$,
$R^7$ and $R^8$ are hydrogen or lower-alkyl,
$R^c$ and $R^e$ are hydrogen Cl, F, Br or $CF_3$,
$R^d$ is hydrogen or $NH_2$, $R^f$ is hydrogen, $CH_3CONH$, $NH_2COCH_2$ or $R^9CH_2CH_2OCH_2CH_2O$ $R^g$ and $R^9$ are phenyl or phenyl substituted by Cl, F or Br.

as well as the physiologically compatible salts thereof.

The term "lower" with reference to alkyl alkoxy, and alkanoyl denotes straight-chain or branched residues with 1 to 6. Preferably 1 to 4, carbon atoms such as, methyl, ethyl, propyl, isopropyl, n-butyl and isobutyl; methoxy, ethoxy, propoxy, isopropoxy, butoxy and isobutoxy; or acetyl, propionyl and butyryl respectively.

The compounds of formula I form salts with acids and these salts also form part of the invention. Examples of such slats are salts with physiologically compatible mineral acids such as hydrochloric acid, hydrobromic acid, sulfuric acid, phosphoric acid; or with organic acids such as oxalic acid, methanesulfonic acid, acetic acid, propionic acid, citric acid, maleic acid, succinic acid, malic acid, fumaric acid, phenylacetic acid or salicylic acid.

The compounds in accordance with the invention contain at least one asymmetric carbon atom and can, therefore, exist as optically active enantiomers as diastereomers or as racemates.

The compounds of formula I in which the residue $R^4$ of group Y is lower-alkoxy or $N(R^7,R^8)$ are preferred, as are those compounds in which n is the integer 1, $R^1$ is hydrogen, $R^2$ is chlorine in the 6-position of a 2-pyridyl residue and Y is phenyl substituted in the p-position by R. Still more preferred compounds are those in which X is hydrogen or a group $X^a$; $R^a$ is hydrogen; Z is 6-chloro-2-pyridyl, and Y is phenyl substituted in the p-position by 2-ethoxyethoxy, 2-phenethoxyethoxy or methoxycarbonylmethoxy. Also preferred are those compounds in which X is a group $X^a$; $R^a$ is hydrogen; Z is phenoxymethyl substituted in the p-Position by carbamoylmethyl, acetamide or 2-phenethoxyethoxy, and Y is p-(2-ethoxyethoxy)phenyl.

Among the above compounds especially preferred are those compounds in which $R^3$ is hydrogen or methyl with the R-configuration. Examples of such compounds are methyl p-[(R)-2-[[(R)-2-(6-chloro-2-pyridyl)-2-hydroxyethyl]amino]propyl]benzoate, methyl P-[(R)-2-[[(R)-2-(6-chloro-2-pyridyl)-2-hydroxyethyl][(S)-m-chloro-β-hydroxyphenethyl]amino]propyl]benzoate, α,α'-[[[(R)-p-(2-ethoxyethoxy)-α-methylphenethyl]imino]dimethylene]bis[(RS)-6-chloro-2-pyridinemethanol], (RS)-6-chloro-α-[[[(R)-P-(2-ethoxyethoxy)-α-methylphenethyl]amino]methyl]-2-pyridinemethanol, α,α'-[[[p-(2-ethoxyethoxy)phenethyl]imino]dimetbylene]bis[(RS)-6-chloro-2-pyridinemethanol], (R)-6-bromo-α-[[[(RS)-2-(6-bromo-2-pyridyl)-2-hydroxyethyl][(R)-p-(2-ethoxyethoxy)-α-methylphenethyl]amino]methyl]-2-pyrimidinemethanol, (R)-6-chloro-α-[[[(S)-2-(6-chloro-2-pyridyl)-2-hydroxyethyl][(R)-α-methyl-p-(2-phenethoxyethoxy)phenethyl]amino]methyl]-2-pyridinemethanol, 2-[p-[(RS)-3-[[(RS)-2-(6-chloro-2-pyridyl)-2-hydroxyethyl][p-(2-ethoxyethoxy)phenethyl]amino]-2-hydroxypropoxy]-p-henyl]acetamide, 4'-[(RS)-3-[[(RS)-2-(6-chloro-2-pyridyl)-2-hydroxyethyl][(R)-p-(2-ethoxyethoxy)-α-methylphenethyl]amino]-2-hydroxypropoxy]acetanilide and 6-chloro-α-[[[(R)-p-(2-ethoxyethoxy)-α-methylphenethyl][(RS)-2-hydroxy-3-[p-[2-(phenethoxy)ethoxy]phenoxy]propyl]amino]methyl]-2-pyridinemethanol.

The compounds in accordance with the invention can be prepared by (a) alkylating an amine of the formula $$(X^1, X^2)NC(H,R^3)(CH_2)_nY \qquad II$$

wherein one of $X^1$ and $X^2$ is hydrogen and the other has one of the significances of X or is the group of the formula

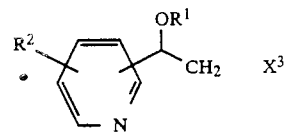

with an agent which introduces the group $X^3$ or one of the groups X and (b) if desired functionally modifying a reactive substituent present in the group Y of the reaction product, if desired esterifying hydroxy groups present in the β-position to the amine nitrogen atom and, if desired, converting a compound of formula I into a salt.

Examples of alkylating agents which can be used in process (a) are compounds of the formula QT, $Z°CHOHCH_2T$, $Z°COCH_2T$ or

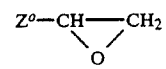

wherein
  Q is X or $X^3$,
  Z° is Z or

and
  T is halogen, especially bromine or chlorine, or a sulfonate group such as methanesulfonate.

The alkylation step (a) can be carried out in a known manner, for example, as described in European Patent applications 101069A1 and 140243A1, conveniently while heating in a suitable solvent. Thus, an amine of formula II and an epoxide of formula III can be reacted at a temperature between 60° C. and the boiling point of the reaction mixture, preferably under an inert atmosphere, such as, argon, in an inert organic solvent, for example, dimethyl sulfoxide (DMSO), acetonitrile, an ether such as tetrahydrofuran (THF) or dioxane or an alcohol such as ethanol. When a halide $Z°CHOHCH_2T$ or $Z°COCH_2T$ is used in place of the epoxide, the reaction can be carried out in an inert organic solvent, such as, a halogenated hydrocarbon, for example, chloroform, at a temperature up to 200° C. When a lower alkyl halide QT is used, the reaction can be carried out in a solvent such as acetonitrile in the presence of a base such as, sodium carbonate at a temperature up to 60° C. When a halide of the formula $Z°COCH_2T$ is used, there is obtained an intermediate in which the keto group $Z°CO$ must be reduced to the alcohol group $Z°CHOH$.

This reaction can be carried out with a complex metal hydride, such as, NaBH₄ in a solvent such as an alkanol, for example, methanol, at about 20°–30° C.

If desired, a reactive substituent which is present in group Y of the reaction product of formula I can be functionally modified in a known manner. Thus, for example a phenol of formula I in which R is hydroxy can be reacted with an agent which introduces group R''. Examples of such agents are compounds of the formula TR'' in which T and R'' have the above significance. This reaction can be carried out in a known manner, for example in a solvent, such as, DMSO, acetone, THF or n-propanol, in the presence of a base, such as, potassium hydroxide, potassium carbonate potassium t-butylate or triethylamine, if desired under argon at a temperature up to the reflux temperature of the reaction mixture.

A lower-carbalkoxy residue present in group Y can be hydrolyzed to the carboxy residue in a known manner, for example, with an acid, such as, hydrochloric acid, sulfuric acid or phosphoric acid or with a base, such as, an alkali metal hydroxide, conveniently at a temperature up to about 110° C. and in a solvent, such as, water or a lower-alkanol, for example, methanol or ethanol, in the case of the acidic hydrolysis, or an aqueous lower-alkanol in the case of the basic hydrolysis.

If desired, one or both hydroxy groups in the β-position to the amine nitrogen atom of an alcohol or diol of formula I can be esterified in a known manner with an agent which introduces one of the groups $R^1$ or $R^a$, for example, with a lower-alkanecarboxylic acid anhydride, such as, acetic anhydride or a benzoyl halide such as, benzoyl chloride.

The amines of formula II and the alkylating agents which can be used in process (a), insofar as they are not known compounds can be prepared in a-known manner. Thus, an epoxyethylpyridine of formula III can be prepared by reaction of the corresponding pyridinecarbaldehyde with trimethylsulfonium methylide in liquid ammonia.

The pyridine-ethanolamine derivatives of formula I in accordance with the invention can be used as active substances in pharmaceutical preparations for the treatment of obesity and/or of diabetes mellitus, especially of obese adult diabetics. In an animal experiment an increased catabolism, primarily of fat, has been demonstrated and observed upon the administration of the pyridine-ethanolamine derivatives of formula I in accordance with the invention. Furthermore it has been demonstrated and observed that the pyridine-ethanolamine derivatives of formula I in accordance with the invention stimulate the formation of brown adipose tissue in rats and obese-hyperglycemic mice. It is known that defects of the brown adipose tissue play a substantial role in the origin of obesity. In obese-hyperglycemic mice and in streptozotocin-diabetic rats the pyridine-ethanolamine derivatives of formula I in accordance with the invention have a pronounced antidiabetic effect in that they have hypoglycemic activity and reduce glycosuria. The pyridine-ethanolamine derivatives of formula I in accordance with the invention exhibit only a slight activity on the working of the heart and circulation. The dosage which can by utilized to administer the compounds of formula I is in the range of from 0.5 to 1000 mg, preferably 2–200 mg per day for an adult warm-blooded animal depending on the strength of activity of the administered compound and on the individual requirements of the patients. The dosage can be administered as a single dosage or in several dosages divided over the day.

In addition in tests with the pyridine-ethanolamine derivatives of formula I in accordance with the invention an increase in the protein content and a decrease in the fat content of the body of a warm-blooded animal could be detected. The pyridine-ethanolamine derivatives of formula I in accordance with the invention therefore lead to an increase in the lean composition of the body at the expense of fat. Accordingly, the pyridine-ethanolamine derivatives of formula I in accordance with the invention can be used above all in medicine for the treatment of conditions which are associated with high protein breakdown, for example, in convalescence after an operation. In this case, the dosages administered lie in the same range as in the treatment of obesity and/or of diabetes mellitus.

The pyridine-ethanolamine derivatives of formula I in accordance with the invention can also be used in the maintenance of fattening animals such as, beef cattle, pigs sheep and poultry. In this case, the dosages administered and the dosage forms administered can be the same as in the case of vitamins. The pyridine-ethanolamine derivatives of formula I in accordance with the invention can also be used as feed additives in dosages in the range of 0.01 to 100 mg/kg depending on the substance, kind of animal and age.

The pharmaceutical preparations contain the active substance together with a compatible pharmaceutical organic or inorganic carrier material, such as, for example, water, gelatine, gum arabic lactose, starch, magnesium stearate, talc, vegetable oils polyalkylene glycols, and the like. The pharmaceutical preparations are preferably administered orally, for example, in the form of tablets, capsules, pills, powders, granulates, solutions, syrups, suspensions, elixirs and the like. The administration can, however, also be carried out parenterally, for example, in the form of sterile solutions, suspensions or emulsions. The pharmaceutical preparations can be sterilized and/or can contain ingredients, such as, preserving agents, stabilizers, wetting agents, emulsifiers, salts for varying the osmotic pressure and buffer substances.

The activity of the compounds of formula I is evident from the test results which follow:

(1) Activity on oxygen consumption

Male albino rats weighing 160–180 g were placed in metabolic cages after fasting for 24 hours. The cages were ventilated with a constant 6 liter room air/minute which was equilibrated at a dew point of 11° C. Samples of the spent air were collected during periods of 14 minutes in each case, after again equilibrating, and the oxygen content and $CO_2$ content were analyzed. After an adaptation time of 4 hours, the animals, divided into groups of 6, received either placebo (5% gum arabic) or the test substance (suspended in 5% gum arabic) per os. Thereafter, the determinations were carried out for a period of 12 hours. In Table I, there is given the percentage of the average oxygen consumption after medication during the first 3 hours and the entire test duration (12 hours) as a percentage of the oxygen consumption of the adaptation period, corresponding corrections for variations in the placebo group having been taken into consideration.

TABLE 1

| Compound prepared in Example No. | Dosage μM/kg | O₂ consumption % of the value of the pre-period | |
|---|---|---|---|
| | | 1st–3rd hour | 1st–12th hour |
| 2Fb | 0.3 | 152 | 121 |
| 4B | 0.1 | 165 | 124 |
| 4C | 0.3 | 180 | 133 |
| 4Fa | 0.1 | 139 | 109 |
| 4G | 0.3 | 123 | 105 |
| 4Ia | 1 | 183 | 137 |
| 4Jb | 1 | 185 | 140 |
| 4Jc | 0.3 | 143 | 117 |
| 4Ka | 0.1 | 158 | 118 |
| 4Kb | 0.3 | 156 | 116 |
| 5a | 0.1 | 139 | 113 |
| 5b | 1 | 172 | 127 |
| 7 | 1 | 156 | 115 |
| 8A | 1 | 176 | 132 |
| 8B | 0.1 | 135 | 107 |
| 9 | 1 | 185 | 143 |
| 11 | 1 | 174 | 134 |

The Examples which follow further illustrate the invention. All temperatures are in degrees Centigrade unless otherwise stated.

EXAMPLE 1

A solution of 1.51 g of p-[(R)-2-aminopropyl]phenol and 1.33 g of 2-(epoxyethyl)pyridine (obtained by the reaction of pyridine-2-carbaldehyde with trimethylsulfonium methylide in liquid ammonia, IR bands at 3056, 3012, 1593, 1474, 1438, 1148, 995, 878, 781 cm$^{-1}$) in 40 ml of DMSO was heated to 100° for 24 hours under argon. The reaction mixture was then evaporated to dryness in a high vacuum at 70° and the residue was chromatographed on silica gel with chloroform/n-propanol/saturated aqueous NH₃ solution (1000:100:5). There were obtained (a) 0.8 g of α,α-[[[(R)-p-hydroxy-α-methylphenethyl]imino]dimethylene]bis[(RS)-2-pyridinemethanol], $[\alpha]_D^{20°} = -21°$ (c=0.3 in MeOH), and (b) 1.4 g of (RS)-α-[[[(R)-p-hydroxy-α-methylphenethyl]amino]methyl]-2-pyridinemethanol, $[\alpha]_D^{20°} = -29°$ (c=0.5 in methanol).

EXAMPLE 2

Analogously to Example 1, 2A) from 1.70 g of 2-chloro-6-epoxyethylpyridine (prepared from 6-chloro-2-pyridinecarbaldehyde by methylenation with dimethylsulfonium methylenide in liquid ammonia, IR bands at 1587, 1563, 1448, 1416, 1158, 1135, 888, 798 cm$^{-1}$) and 1.51 g of p-[(R)-2-amino-propyl]phenol there were obtained (a) 0.94 g of α,α'-[[[(R)-p-hydroxy-α-methylphenethyl]imino]dimethylene]bis[(RS)-6-chloro-2-pyridinemethanol], $]\alpha]_D^{20°} = -21°$ (c=0.5 in MeOH), and (b) 2.3 g of (RS)-α-[[[(R)-α-hydroxy-p-methylphenethyl]amino]methyl]-6-chloro-2-pyridinemethanol, $[\alpha]_D^{20°} -24°$ (c=0.5 in methanol).

(2B) from 1.60 g of 2-epoxyethylpyridine and 1.50 g of tyramine there were obtained (a) 0.84 g of α,α'-[[[p-hydroxy-phenethyl]imino]-dimethylene]bis[(RS)-2-pyridinemethanol], IR bands at 1612, 1596, 1571, 1515, 1242, 1106, 1075, 826 and 770 cm$^{-1}$, and (b) 1.34 g of (RS)-α-[[[p-hydroxyphenethyl]amino]-methyl]-2-pyridinemethanol, IR bands at 1612, 1594, 1571, 1515, 1250, 828, 769 cm$^{-1}$, (2C) from 1.71 g of 2-chloro-6-epoxyethylpyridine and 1.51 g of tyramine there were obtained (a) 1.1 g of α,α'-[[[p-hydroxyphenethyl]imino]dimethylene]bis[(RS)-6-chloro-2-pyridinemethanol], IR bands at 3276, 1613, 1585, 1561, 1515, 1232, 829, 798 cm$^{-1}$, and (b) 1.9 g of (RS)-6-chloro-E-[[[p-hydroxyphenethyl]amino]methyl]-2-pyridinemethanol, IR bands at 1612, 1585, 1561, 1515, 1252, 1158, 1138, 1108, 1047, 828, 798 cm$^{-1}$, (2D) from 3.0 g of p-[(R)-2-aminopropyl]phenol and 6.0 g of 2-bromo-6-epoxyethylpyridine (prepared by the reaction of 2-bromopyridine-6-carbaldehyde with trimethylsulfonium methylide in liquid ammonia, IR bands at 1585, 1556, 1444, 1412, 1159, 1119, 882, 796 cm$^{-1}$), there were obtained (a) 7.39 g of α,α'-[[[(R)-p-hydroxy-α-methylphenethyl]imino]dimethylene]bis[(RS)-6-bromo-2-pyridinemethanol], $[\alpha]_D^{20°} = -13°$ (c=0.7 in MeOH), and (b) 2.0 g of (RS)-α-[[[(R)-p-hydroxy-α-methylphenethyl]amino]methyl]-6-bromo-2-pyridinemethanol, $[\alpha]_D^{20°} = -19°$ (c=1.0 in MeOH), (2E) from 3.6 g of 2-chloro-6-epoxyethylpyridine and 3.3 g of p-[(R)-3-aminobutyl]phenol there were obtained (a) 2.50 g of α,α'-[[[(R)-3-(p-hydroxyphenyl)-1-methylpropyl]imino]dimethylene]bis[(RS)-6-chloro-2-pyridinemethanol], $[\alpha]_D^{20°} = +62$V (c=0.7 in MeOH), and (b) 3.5 g of (RS)-6-chloro-α-[[[(R)-3-(p-hydroxyphenyl)-1-methylpropyl]amino]methyl]-2-pyridinemethanol, $[\alpha]_D^{20°} = +4°$ (c=0.6 in MeOH), (2F) from 2-chloro-6-epoxyethylpyridine and methyl p-[(R)-2-aminopropyl]benzoate there were obtained (a) methyl p-[(R)-2-[[(R)-2-(6-chloro-2-pyridyl)-2-hydroxyethyl]amino]propyl]benzoate, m.p. 140°–142° (from methylene chloride-hexane), $[\alpha]_D^{20°} + +38°$ (c=0.4 in MeOH), (b) methyl p-[(R)-2-[[(R)-2-(6-chloro-2-pyridyl)-2-hydroxyethyl]amino]propyl]benzoate, m.p. 67°–68° (from ether), $[\alpha]_D^{20°} = -73°$ (c=0.7 in MeOH), and (c) methyl p-[(R)-2-[bis[(RS)-2-(6-chloro-2-pyridyl)-2-hydroxyethyl]amino]propyl]benzoate, $[\alpha]_D^{20°} = -33°$ (c=0.3 in methanol), 2 (G) from 2-chloro-6-epoxyethylpyridine and methyl p-[(R)-2-aminopropyl]-β-methylcinnamate here were obtained (a) methyl p-[(R)-2-[[(R)-2-(6-chloro-2-pyridyl)-2-hydroxyethyl]amino]propyl-β-methylcinnamate oxalate, m.p. 127°–129°, $[\alpha]_D^{20°} = -39°$ (c=0.9 in methanol).

(b) methyl p-[(R)-2-[[(S)-2-(6-chloro-2-pyridyl)-2-hydroxyethyl]amino]propyl]-β-methylcinnamate, m.p. 101°–102°, $[\alpha]_D^{20°} = -41°$ (c=0.4 in MeOH), and (c) methyl p-[(R)-2-[bis[(RS)-2-(6-chloro-2-pyridyl)-2-hydroxyethyl]amino]propyl]-β-methylcinnamate, $[\alpha]_D^{20°} = -26°$ (c=0.3 in MeOH), (2H) from 1.0 g of (R)-1-methyl-3-(4-aminocarbonylphenyl)-propylamine and 695 mg of 2-(epoxyethyl)pyridine there were obtained (a) 200 mg of α,α-[[[(R)-3-(p-carbamoylphenyl)-1-methylpropyl]imino]dimethylene]bis[(RS)-2-pyridinemethanol], $[\alpha]_D^{20°} = 1.0$ in MeOH), and (b) 829 mg of p-[(R)-3-[[(RS)-β-hydroxy-2-pyridylethyl]-amino]butyl]benzamide, $[\alpha]_D^{20°} = +10°$ (c=1.0 in MeOH);

(2I) from 1.0 g of (R)-1-methyl-3-(4-aminocarbonyl-phenyl)-propylamine and 695 mg of 4-(epoxyethyl)pyridine there were obtained 480 mg of p-[(R)-3-[[(RS)-8-hydroxy-4-pyridylethyl]amino]butyl]benzamide, $[\alpha]_D^{20°} = +6°$ (c=1.0 in MeOH).

EXAMPLE 3

A solution of 500 mg of (RS)-α-[[[(R)-p-hydroxy-α-methylphenethyl]amino]methyl]-2-pyridinemethanol (Example 1b), 280 mg of 2-ethoxyethyl methanesulfonate and 185 mg of KOH in 20 ml of n-propanol was heated to reflux under argon for 24 hours For the working-up, the mixture was poured into ice-water and extracted with ethyl acetate. The organic phase was washed with water, dried with $Na_2SO_4$ and evaporated to dryness in a vacuum. The residue was chromatographed on $SiO_2$. With chloroform/n-propanol/aq. sat. $NH_3$ solution (1000:20:2) there were eluted 340 mg of (RS)-α-[[[(R)-p-(2-ethoxyethoxy)-α-methylphenethyl]amino]methyl]-2-pyridinemethanol, $[\alpha]_D^{20°} = -20°$ (c=0.3 in methanol).

EXAMPLE 4

Analogously to Example 3, (4A) from 600 mg of α,α'-[[[(R)-p-hydroxy-α-methylphenethyl]imino]dimethylene]bis[(RS)-2-pyridinemethanol](Example 1a) and 282 mg of 2-ethoxyethyl methanesulfonate there were obtained 325 mg of α,α'-[[[-(R)-p-(2-ethoxy-ethoxy)-α-methylphenethyl]imino]dimethylene]bis[(RS)-2-pyridinemethanol], $[\alpha]_D^{20°} = -23°$ (c=0.5 in methanol), (4B) from 810 mg of α,α'-[[[(R)-p-hydroxy-α-methylphenethyl]imino]dimethylene]bis[(RS)-6-chloro-2-pyridinemethanol] (Example 2Aa) and 336 mg of 2-ethoxyethyl methanesulfonate there were obtained 450 mg of α,α'-[[[(R)-p-(2-ethoxyethoxy)-α-methylphenethyl]imino]dimethylene]bis[(RS)-6-chloro-2-pyridinemethanol], $[\alpha]_D^{20°} = -23°$ (c =0.5 in MeOH), (4C) from 1.0 g of (RS)-α-[[[(R)-p-hydroxy-α-methylphenethyl]amino]methyl]-6-chloro-2-pyridinemethanol (Example 2Ab) and 610 mg of 2-(R)epoxyhyl methanesulfonate there were obtained 900 mg of (RS)-6-chloro-α-[[(R)-p-(2-ethoxyethoxy)-α-methylphenethyl]amino]methyl]-2-pyridinemethanol, $[\alpha]_D^{20°} = -19°$ (c =1.0 in MeOH), (4D) from 1.23 g of (RS)-α-[[[p-hydroxyphenethyl]amino]methyl]-2-pyridinemethanol (Example 2Bb) and 0.95 g of 2-ethoxyethyl methanesulfonate there were obtained (a) 0.64 g of (RS)-α-[[[p-(2-ethoxyethoxy)phenethyl]amino]methyl]-2-pyridinemethanol, IR bands at 3296, 1611, 1591, 1571, 1511 cm$^{-1}$, and (b) 280 mg of (RS)-α-[[(2-ethoxyethyl)[p-(2-ethoxyethoxy)phenethyl]amino]methyl]-2-pyridinemethanol, IR bands at 3414, 1610, 1590, 1571, 1511, 1246, 1120, 1065, 823, 770 cm$^{-1}$, (4E) from 780 mg of α,α'-[[[p-hydroxyphenethyl]imino]-dimethylene]bis[(RS)-2-pyridinemethanol] (Example 2Ba) and 368 mg of 2-ethoxyethyl methanesulfonate there were obtained 540 mg of α,α'-[[[p-(2-ethoxyethoxy)phenethyl]imino]dimethylene]bis[(RS)-2-pyridinemethanol], IR bands at 3364, 3233, 1610, 1591, 1571, 1511, 1245, 1123, 1067, 823, 771 cm$^{-1}$, (4F) from 830 mg of (RS)-6-chloro-α-[[[p-hydroxyphenethyl]amino]methyl]-2-pyridinemethanol (Example 2Cb) and 584 mg of 2-ethoxyethyl methanesulfonate there were obtained a) 500 mg of (RS)-6-chloro-α-[[[p-(2-ethoxyethoxy)-phenethyl]amino]methyl]-2-pyridinemethanol, IR bands at 2927, 2870, 1610, 1583, 1561, 1511, 1438, 1247, 1121, 800 cm$^{-1}$, and (b) 252 mg of (RS)-6-chloro-α-[(2-ethoxyethyl)[p-(2-ethoxyethoxy)phenethyl]amino]methyl]-2-pyridinemethanol, IR bands at 3410, 2868, 1611, 1584, 1561, 1511, 1246, 1124, 1065, 824, 799 cm$^{-1}$, (4G) from 1.0 g of α,α'-[[[p-hydroxyphenethyl]imino]dimethylene]bis[(RS)-6-chloro-2-pyridinemethanol] (Example 2Ca) and 433 mg of 2-ethoxyethyl methanesulfonate there were obtained 520 mg of α,α'-[[[p-(2-ethoxyethoxy)-phenethyl], imino]dimethylene]-bis[(RS)-6-chloro-2-pyridinemethanol]IR bands at 3385, 1610 1584, 1561. 1511, 1245, 1157, 1133, 825, 799 cm$^{-1}$, (4H) from 1.80 g of (RS)-α-[[[(R)-p-hydroxy-α-methylphenethyl]amino]methyl]-6-bromo-2-pyridinemethanol (Example 2Db) and 1.14 g of 2-ethoxyethyl methanesulfonate there were obtained 1.1 g of (RS)-6-bromo-α-[[[(R) -p-(2-ethoxyethoxy)-α-methylphenethyl]amino]methyl]-2-pyridinemethanol, m.p. 71° (from acetone-hexane), $[\alpha]_D^{20°} = -5°$ (c=0.5 in methanol), (4I) from 6.7 g of α,α'-[[[(R)-p-hydroxy-α-phenethyl]imino]dimethylene]bis[(RS)-6-bromo-2-pyridinemethanol] (Example 2Da) and 2.35 g of 2-ethoxyethyl methanesulfonate there were obtained (a) 2.0 g of (R)-6-bromo-α-[[[(RS)-2-(6-bromo-2-pyridyl)-2-hydroxyethyl][(R)-p-(2-ethoxyethoxy)-α-methylphenethyl]amino]methyl]-2-pyridinemethanol, $[\alpha]_D^{20°} = -61°$ (c=1.0 in MeOH), diastereomer ratio RSR:RRR =2:1, and (b) 1.0 g of α,α'-[[[(R)-p-(2-ethoxyethoxy)-α-methylphenethyl]imino]dimethylene]bis-[(S)-6-bromo-2-pyridinemethanol], $[\alpha]_D^{20} = +58°$ (c=1.0 in MeOH), (4J) from 2.3 g of α,α'-[[[(R)-p-hydroxy-α-methylphenethyl]imino]dimethylene]bis[(RS)-6-chloro-2-pyridinemethanol] (Example 2Aa) and 1.47 g of 2-phenethoxyethyl methanesulfonate there were obtained (a) 360 mg of α,α'-[[[(R)-p-(2-phenethoxyethoxy)-α-methylphenethyl]imino]dimethylene]bis[(R)-6-chloro-2-pyridinemethanol], $[\alpha]_D^{20°} = -94°$ (c=1.0 in MeOH), (b) 590 mg of (R)-6-chloro-α-[[[(S)-2-(6-chloro-2-pyridyl)-2-hydroxyethyl] [(R)-α-methyl-p-(2-phenethoxyethoxy)phenethyl]amino]methyl]-2-pyridinemethanol, $[\alpha]_D^{20°} = -48°$ (c=1.0 in MeOH), and (c) 520 mg of α,α'-[[[(R)-p-[2-(phenethoxy)ethoxy]-α-methylphenethyl]imino]dimethylene]bis[(S)-6-chloro-2-pyridinemethanol], $[\alpha]_D^{20°} = +31°$ (c=1.0 in MeOH), (4K) from 3.0 g of α,α'-[[[(R)-p-hydroxy-α-methylphenethyl]imino]dimethylene]bis[(RS)-6-chloro-2-pyridinemethanol] (Example 2Aa) there were obtained (a) 869 mg of the 1:2 mixture of α,α'-[[[(R)-p-(2-ethoxyethoxy)-α-methylphenethyl]imino]dimethylene]-bis-(R)-6-chloro-2-pyridinemethanol] and (R)-α-[[[(S)-2-(6-chloro-2-pyridyl)-2-hydroxyethyl][(R)-p-(2-ethoxyethoxy)-α-methylphenethyl]amino]methyl]-2-pyridinemethanol, $[\alpha]_D^{20°} = -62°$ (c=0.3 in methanol), and (b) 280 mg of α,α'-[[[(R)-p-(2-ethoxyethoxy)-α-methylphenethyl)imino]dimethylene]bis[(S)-6-chloro-2-pyridinemethanol], $[\alpha]_D^{20°} = +43°$ (c=0.4 in methanol).

(4L) from 1.60 g of (RS)-6-chloro-α-[[[(R)-3-(p-hydroxyphenyl)-1-methylpropyl]amino]methyl]-2-pyridinemethanol (Example 2Eb) there was obtained 0.970 g of (RS)-6-chloro-α-[[[(R)-3-(2-ethoxyethoxy)- phenyl]-1-methylpropyl]-amino]methyl]-2-pyridinemethanol, m.p. 66°, $[\alpha]_D^{20°} = +6°$ (c=0.8 MeOH).

EXAMPLE 5

A solution of 2.15 g of α,α'-[[[(R)-p-hydroxy-α-methylphenethyl]imino]dimethylene]bis[(RS)-6-chloro-2-pyridinemethanol] (Example 2Aa) in 95 ml of acetone was stirred at room temperature for 5 hours under argon after the addition of 314 g of powdered KOH, 860 mg of methyl bromoacetate and a trace of potassium iodide. For the working-up, the mixture was poured into ice-water and extracted with ethyl acetate. The organic extract was washed neutral with water, dried with sodium sulfate and evaporated in a vacuum. The residue was chromatographed on 300 g of $SiO_2$. With chloroform/hexane/n-propanol/sat. $NH_3$ solution (1000:1000:5:0.5) there were firstly eluted (a) 600 mg of methyl [p-[(R)-2-[bis[(RS)-2-(6-chloro-2--pyridyl)-2-hydroxyethyl]amino]propyl]phenoxy]acetate, $[\alpha]_D^{20°} = -70°$ (c=1.0 in methanol).

(b) The further fractions yielded 310 mg of methyl [p-[(R)-2-[bis[(S)-2-(6-chloro-2-pyridyl)-2-hydroxyethyl]amino]propyl]phenoxy]acetate, $[\alpha]_D^{20°} = +17°$ (c=1.0 in methanol).

EXAMPLE 6

Analogously to Example 5, from α,α'-[[[(R)-3-(p-hydroxyphenyl)-1-methylpropyl]imino]dimethylene]-bis[(RS)-6-chloro-2-pyridinemethanol](Example 2Ea) there were obtained (a) methyl [p-[(R)-3-[bis[(RS)-2-(6-chloro-2-pyridyl)-2-hydroxyethyl]amino]butyl]phenoxy]acetate, $[\alpha]_D^{20°} = -24°$ (c=0.5 m MeOH), and (b) methyl [p-[(R)-3-[bis[(R)-2-(6-chloro-2-pyridyl)-2-hydroxyethyl]amino]butyl]phenoxy]acetate, $[\alpha]_D^{20°} = -112°$ (c =0.2 in MeOH).

EXAMPLE 7

A mixture of 800 mg of (RS)-6-chloro-α-[[[p-(2-ethoxyethoxy)phenethyl]amino]methyl]-2-pyridinemethanol (Example 4Fa), 40 ml of DMSO and 912 mg of 2-[p-(2,3 -epoxypropoxy)phenyl]acetamide was heated to 100° for 18 hours while stirring The reaction mixture was evaporated to dryness in a vacuum and the residue was chromatographed on silica gel. With chloroform/n-propanol/sat. aq. $NH_3$ (1000:20:2) there could be eluted 690 mg of 2-[p-(RS)-3-[[(RS)-2-(6-chloro-2-pyridyl)-2-hydroxyethyl][p-(2-ethoxyethoxy)phenethyl]amino]-2-hydroxypropoxy]phenyl]acetamide, IR bands at 3347, 3203, 1668, 1611 1584, 1561, 1511, 1246, 1124, 822, 800 cm$^{-1}$.

EXAMPLE 8

Analogously to Example 7, (A) using 4'-(2,3-epoxypropoxy)acetanilide there were obtained from 1.0 g of (RS)-6-chloro-α-[[[(R)-p-(2-ethoxyethoxy)-α-methylphenethyl]amino]methyl]-2-pyridinemethanol (Example 4C) 530 mg of 4'-[(RS)-3-[[(RS)-2-(6-chloro-2-pyridyl)-2-hydroxyethyl][(R)-p-(2-ethoxyethoxy)-α-methylphenethyl]amino]-2-hydroxypropoxy]acetanilide, $[\alpha]_D^{20°} = -39'$ (c=0.4 in MeOH), (B) using 1.2-epoxy-3-[p-[2-(phenethoxy)ethoxy]-phenoxy]propane there were obtained from 1.0 g of (RS)-6-chloro-α-[[[(R)-p-(2-ethoxyethoxy)-α-methylphenethyl]-amino]methyl]-2-pyridinemethanol (Example 4C) 260 mg of 6-chloro-α-[[[(R)-p-(2-ethoxyethoxy)-α-methylphenethyl][(RS)-2-hydroxy-3-[p-[2-(phenethoxy)ethoxy]phenoxy]propyl]amino]methyl-2-pyridinemethanol, $[\alpha]_D^{20°} = -41°$ (c=0.3 in MeOH), (C) from 500 mg of methyl p-[(R)-2-[[(R)-2-(6-chloro-2-pyridyl)-2-hydroxyethyl]amino]propyl]benzoate (Example 2Fb) and 442 mg of (S)-3-chlorostyrene oxide there were obtained 280 mg of methyl p-[(R)-2-[[(R)-2-(6-chloro-2-pyridyl)-2-hydroxyethyl][(S)-m-chloro-β-hydroxyphenethyl]amino]propyl]benzoate, $[\alpha]_D^{20°} = -59°$ (c=0.5 MeOH).

EXAMPLE 9

1.56 g of 4-amino-3,5-dichlorophenacyl bromide were added portionwise within 30 minutes to a solution, heated to 50°, of 1.89 g of (RS)-6-chloro-α-[[[(R)-p-(2-ethoxyethoxy)-α-methylphenethyl]amino]methyl]-2-pyridinemethanol (Example 4C) in 100 ml of chloroform and the mixture was subsequently heated to reflux for an additional 20 hours. The reaction mixture was then concentrated to dryness in a vacuum. The residue was dissolved in 75 ml of methanol treated with 25 ml of water and the solution was cooled to 5°. A solution of 400 mg of sodium borohydride in 5 ml of water was added dropwise at 0°-5° and the reaction mixture was stirred for 90 minutes. For the working-up, the mixture was poured into ice-water and extracted three times with methylene chloride. The organic extracts were washed with water, dried with $Na_2SO_4$ and evaporated in a vacuum. There were obtained 2.9 g of crude product which was chromatographed on 200 g of silica gel. With hexane/acetone 4:1 there could be eluted 850 mg of (RS)-α-[[[(RS)-4-amino-3,5-dichloro-β-hydroxyphen-ethyl][(R)-p-(2-ethoxyethoxy)-α-methylphenethyl]amino]-methyl]-6-chloro-2-pyridinemethanol, $[\alpha]_D^{20°} = -39°$ (c=0.5 in MeOH).

EXAMPLE 10

A mixture of 900 mg of (RS)-6-chloro-α-[[[p-(2-ethoxyethoxy)phenethyl]amino]methyl]-2-pyridinemethanol (Example 4Fa) 25 ml of acetonitrile 0.41 ml of ethyl iodide and 262 mg of sodium carbonate was heated to 50° while stirring for 7 hours. After the addition of 0.21 ml of ethyl iodide, the mixture was heated to 50° for 44 hours. For the working-up the reaction mixture was filtered and the filtrate was evaporated to dryness in a vacuum. The residue was chromatographed on 50 g of silica gel. With chloroform/n-propanol/sat. aq. $NH_3$ (1000:10:1) there could be eluted 700 mg of (RS)-6-chloro-α-[[ethyl-[p-(2-ethoxyethoxy)-phenethyl]amino]methyl]-2-pyridinemethanol, IR bands at 3426 1611, 1584, 1562, 1511 1246, 1127, 822 800 cm$^{-1}$.

EXAMPLE 11

Analogously to Example 10 but using methyl iodide in place of ethyl iodide, from 870 mg of (RS)-6-chloro-α-[[[(R)-p-(2-ethoxyethoxy)α-methylphenethyl]amino]-methyl]-2-pyridinemethanol (Example 4C) there were obtained 580 mg of (RS)-6-chloro-α-[[[(R)-p-(2-ethoxyethoxy)-α-methylphenethyl)methyl]amino]methyl]-2-pyridinemethanol, $[\alpha]_D^{20°} = -8.5°$ (c=0.4 in MeOH).

EXAMPLE 12 c A mixture of 1.39 g of α,α'-[[[(R)-p-hydroxy-α-methylphenethyl]imino]dimetbylene]bis[(RS)-6-chloro-2- pyridinemethanol] (Example 2Aa). 600 mg of 6-bromo-1-hexanol, 370 mg of potassium t-butylate and 15 ml of DMSO was stirred at room temperature for 90 minutes under argon. For the working-up, the mixture was evaporated in a vacuum and the residue was chromatographed on SiO$_2$. There were isolated:

(a) 440 mg of α,α'-[[[(R)-p-(6-hydroxyhexyloxy)-α-methylphenethyl]imino]dimethylene]bis[(RS)-6-chloro-2-pyridinemethanol], $[α]_D^{20°} = -18°$ (c=0.3 in methanol), and (b) 370 mg of (RS)-6-chloro-α-[[[(RS)-2-(6-chloro-2-pyridyl)-2-(6-hydroxyhexyloxy)ethyl]][(R)-p-(6-hydroxyhexyloxy)-α-methylphenethyl]amino]methyl]-2-pyridinemethanol, $[α]_D^{20°} = -21°$ (c=0.5 in MeOH).

EXAMPLE 13

A solution of 0.50 g of α,α'-[[[(R)-p-hydroy-α-methylphenethyl]imino]dimethylene]bis[(RS)-6-chloro-2-pyridinemethanol] (Example 2Aa) in 5 ml of pyridine and 5 ml of acetic anhydride was held at room temperature for 2 hours. The reaction mixture was then evaporated in a vacuum and the residue was chromatographed over silica gel. There were obtained 480 mg of p-acetoxy-[(R)-2-[bis[(RS)-2-chloro-2-pyridyl)-2-acetoxyethyl]amino]-propyl]benzene, $[α]_D^{20°} = -34°$ (c=0.6 in MeOH).

EXAMPLE 14

484 mg of 3-[(RS)-2-oxiranyl]pyridine and 549 mg of tyramine were boiled under reflux in 10 ml of acetonitrile for 20 hours. The reaction mixture was evaporated to dryness in a vacuum and the residue was chromatographed on silica qel with MeOH. After decolorization with active carbon and crystallization from acetonitrile there were obtained 200 mg of (RS)-α-[[(p-hydroxyphenethyl)amino]methyl]-2-pyridinemethanol, m.p. 112°-114°.

EXAMPLE 15

Analogously to Example 14, (A) from 1.3 g of p-(2-ethoxyethoxy)-phenethylamine (prepared by the reaction of N-carbobenzoxytyramine in DMSO in the presence of potassium hydroxide with ethoxyethyl methanesulfonate and catalytic hydrogenation of the benzyl [p-(2-ethoxyethoxy)]phenethylcarbamate obtained in methanol in the presence of pd/C) and 726 mg of 3-[(RS)-2-oxiranyl]pyridine there were obtained (a) 670 mg of (RS)-α-[[[p-(2-ethoxyethoxy)phenethyl]amino]methyl]-3-pyridinemethanol, $ε_{224}=11900$, $ε_{261}=3200$, and (b) 150 mg of α,α'-[[[p-(2-ethoxyethoxy)phenethyl]imino]dimethylene]bis[(RS)-3-pyridinemethanol], NMR (in CDCl$_3$) 1.23 ppm (t) CH$_2$-CH$_3$; 2.6–3.1 ppm (m) CH$_2$N, CH$_2$Ar; 3.59 ppm (q) CH$_2$-CH$_3$; 3.77 and 4.10 ppm (t) O—CH$_2$—CH$_2$—O; 4.75 ppm (m) CH—OH; 6.9: 7.1: 7.26: 7.7; 8.5 ppm (m) arom. H, (B) from 309 mg of 3-[(RS)-2-oxiranyl]pyridine and 570 mg of (R)-p-(2-ethoxethoxy)-α-methylphenethylamine—prepared by the reaction of (R)-p-hydroxy-α-methylphenethylamine with benzyl chloroformate in dioxane and water in the presence of sodium bicarbonate, reaction of the (R)-N-carbenzoxy-p-hydroxy-α-methylphenethylamine obtained in DMSO with chloroethyl ether and potassium hydroxide followed by catalytic hydrogenation of the (R)-benzyl [p-(2-ethoxyethoxy)-α-methylphenethylcarbamate obtained in MeOH in the presence of pd/C - there were obtained 248 mg of (RS)-α-[[[(R)-p-(2-ethoxyethoxy)-α-methylphenethyl]amino]methyl]-3-pyridinemethanol, $[α]_D^{20°} = -23 2°$ (0.4% in MeOH).

EXAMPLE 16

606 mg of 3-[(RS)-2-oxiranyl]pyridine and 991 mg of (RS)-5-(3-aminobutyl)-2-thiophenecarboxamide were heated to 100° for 25 hours in 5 ml of DMSO. The reaction mixture was diluted with water and extracted three times with methylene chloride. The methylene chloride solutions were washed with water, dried and evaporated in a vacuum. Chromatography of the residue on silica gel with ether/methanol gave 149 mg of 5-[(RS)-3-[[(RS)-2-hydroxy-2-(3-pyridyl)ethyl]amino]butyl]-2-thiophenecarboxamide, $ε_{201}=14420$; $ε_{268}=11310$.

EXAMPLE 17

(A) 778 mg of 2-chloro-6-[(RS)-epoxyethyl]pyridine and 1.34 g of ethyl (E)-5-[(RS)-3-aminobutyl]-⊕-methyl-2-thiopheneacrylate were stirred at 100° in 5 ml of DMSO for 15.5 hours. The reaction mixture was diluted with water and extracted three times with methylene chloride. The methylene chloride solutions were washed with water and sodium chloride solution, dried and evaporated in vacuo. The residue was chromatographed on silica gel. Ether eluted 481 mg of ethyl (E)-5-[(RS)-3-[bis[(RS)-2-(6-chloro-2-pyridyl)-2-hydroxyethyl]amino]butyl]-β-methyl-2-thiopheneacrylate, $ε_{211}=21650$, $ε_{268}=13230$, $ε_{322}=17540$.

(B) Ether/methanol 9:1 subsequently eluted 1.14 g of ethyl (E)-5-(RS)-3-[[(RS)-2-(6-chloro-2-pyridyl)-2-hydroxyethyl]amino]butyl]-β-methyl-2-thiopheneacrylate, $ε_{213}=16500$, $ε_{267}=9710$, $ε_{321}=17740$.

EXAMPLE 18

Analogously to Example 17, from 1.01 g of 3-[(RS)-2-oxiranyl]pyridine an 2.23 g of ethyl (E)-5-[(RS)-3-aminobutyl]-β-methyl-2-thiopheneacrylate there were obtained 1.13 g of ethyl (E)-5-[(RS)-3-[[(RS)-2-hydroxy-2-(3-pyridyl)ethyl]amino]butyl]-β-methyl-2-thiopheneacrylate, $ε_{202}=13510$, $ε_{261}=6750$, $ε_{267}=6630$, $ε_{320}=16450$.

EXAMPLE 19

Analogously to Example 17 there were obtained (A) ethyl (E)-5-[(RS)-2-[bis[(RS)-2-(6-chloro-2-pyridyl)-2-hydroxyethyl]amino]propyl]-β-methyl-2-thiopheneacrylate. $ε_{210}=22270$, $ε_{268}=13820$, $ε_{325}=17800$, (B) ethyl (E)-5-[(RS)-2-[[(RS)-2-(6-chloro-2-pyridyl)-2-hydroxyethyl]amino]propyl]-β-methyl-2-thiopheneacrylate. $ε_{212}=16640$, $ε_{267}=9720$, $ε_{319}=17670$, (C) (RS)-4-chloro-α-[[[p-(2-ethoxyethoxy)phenethyl]amino]methyl]-2-pyridinemethanol, $ε_{268}=3880$, and (D) α,α'-[[[p-(2-ethoxyethoxy)phenethyl]imino]dimethylene]bis[(RS)-4-chloro-2-pyridinemethanol], $ε_{262}=663$, $ε_{269}=6380$.

The 4-chloro-2-(2-oxiranyl)pyridine, $ε_{201}=15240$, $ε_{263}=2850$, $ε_{268}=460$, used as the starting material was prepared by the reaction of 4-chloro-2-pyridinealdehyde with trimethylsulfoniummethyl sulfate in a mixture of methylene chloride and 50% sodium hydroxide solution.

EXAMPLE 20

(RS)-2-Chloro-α-[[[(p-(2-ethoxyethoxy)phenethyl]amino]methyl]-4-pyridinemethanol, m.p. 76°-78° C.; $ε_{201}=25940$, $ε_{224}=13300$, $ε_{263}=3740$, $ε_{269}=3690$, was obtained analogously to Example 14.

The 2-chloro-4-(2-oxiranyl)pyridine, $\epsilon_{201}=15080$, $\epsilon_{265}=2790$, used as the starting material was prepared by reducing methyl 2-chloroisonicotinate with diisobutylaluminum hydride in toluene and reacting the resulting 2-chloroisonicotinic aldehyde m.p. 46°–48° C.; $\epsilon_{264}=2810$, $\epsilon_{200}=950$, with trimethylsulfoniummethyl sulfate in methylene chloride/50% NaOH.

EXAMPLE 21

(A) A solution of 958 mg of methyl p-[(R)-2-[[(R)-2-(6-chloro-2-pyridyl)-2-hydroxyethyl]amino]propyl]-β-methylcinnamate oxalate (Example 2Ga), 60 ml of 5% methanolic KOH and 10 ml of water were heated to 50° under argon while stirring for 3 hours. For the working-up, the mixture was diluted with water, adjusted to pH 5 with 2N hydrochloric acid and extracted repeatedly with ethyl acetate, The combined extracts were dried and evaporated in a vacuum. There were obtained 550 mg of amorphous p-[(R)-2-[[(R)-2-(6-chloro-2-pyridyl)-2-hydroxyethyl]amino]propyl]-β-methylcinnamic acid hydrochloride $[E]_D^{20}32 = 45°$ (c=0.5 in MeOH).

(B) Analogously to Example 21A. from 697 mg of methyl p-[(R)-2-[[(S)-2-(6-chloro-2-pyridyl)-2-hydroxyethyl]amino]propyl]benzoate there were obtained 420 mg of amorphous p-[(R)-2-[[(S)-2-(6-chloro-2-pyridyl)-2-hydroxyethyl]amino]propyl]benzoic acid hydrochloride, $[\alpha]_D^{20}=+33°$ (c =0.5 in MeOH).

EXAMPLE 22

Tablets of the following composition are prepared in the usual manner:

| Active substance of formula I, for example. | |
|---|---|
| (RS)-6-chloro-α-[[[(R)-p-(2-ethoxyethoxy)-α-methylphenethyl]-amino]methyl]-2-pyridinemethanol | 250 mg |
| Lactose | 200 mg |
| Maize starch | 300 mg |
| Maize starch paste | 50 mg |
| Calcium stearate | 5 mg |
| Dicalcium phosphate | 45 mg |

We claim:
1. A compound of the formula

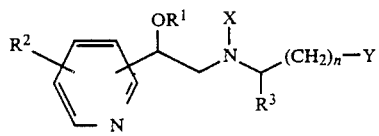

I wherein
n is 1 or 2
X is a group $X^a$ of the formula

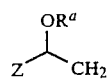

$X^a$

Z is a group of the formula

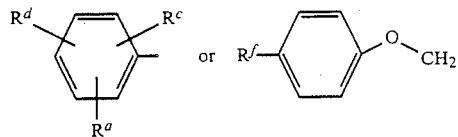

Y is

R is $R^o$ or $OR''$
$R^o$ is lower-alkyl, $COR^4$ or $C(R^5)=CHCOR^4$,
R'' is hydrogen, lower-alkyl, lower-alkanoyl, $(CH_2)_{1-6}$—OH, $(CH_2)_{1-6}$—$O(CH_2)_{1-6}$—$R^6$ or $(CH_2)_{1-6}$—$COR^4$
$R^1$ and $R^a$ are hydrogen, lower-alkanoyl, benzoyl or $(CH_2)_{1-6}$—OH
$R^2$ is hydrogen, Cl, Br or $CF_3$,
$R^3$ and $R^5$ are hydrogen or $CH_3$,
$R^4$ is hydroxy, lower-alkoxy or $N(R^7, R^8)$,
$R^6$ is hydrogen, $R^g$, OH or $COR^4$,
$R^7$ and $R^8$ are hydrogen or lower-alkyl,
$R^c$ and $R^e$ are hydrogen, Cl, F, Br or $CF_3$,
$R^d$ is hydrogen or $NH_2$,
$R^f$ is hydrogen, $CH_3CONH$, $NH_2COCH_2$ or $R^9CH_2CH_2OCH_2CH_2O$,
$R^g$ and $R^9$ are phenyl or phenyl substituted by Cl, F or Br,
an enantiomer, diastereomer or racemate thereof or a physiologically compatible salt thereof.

2. A compound according to claim 1, wherein $R^4$ in the group Y is lower-alkoxy or $N(R^7, R^8)$.

3. A compound according to claim 2, wherein n is the integer 1, $R^1$ is hydrogen, $R^2$ is chlorine in the 6-position of a 2-pyridyl residue and Y is phenyl substituted in the p-position by R.

4. A compound according to claim 3, wherein X is $X^a$; $R^a$ is hydrogen; Z is phenoxymethyl substituted in the p-position by carbamoylmethyl, acetamide or 2-phenethoxyethoxy, and Y is p-(2-ethoxyethoxy)phenyl.

5. A compound according to claim 4, wherein $R^3$ is hydrogen or methyl with the R-configuration.

6. A compound according to claim 1, methyl p-[(R)-2-[[(R)-2-(6-chloro-2-pyridyl)-2-hydroxyethyl][(S)-m-chloro-β-hydroxyphenethyl]amino]propyl]benzoate, represented by the formula

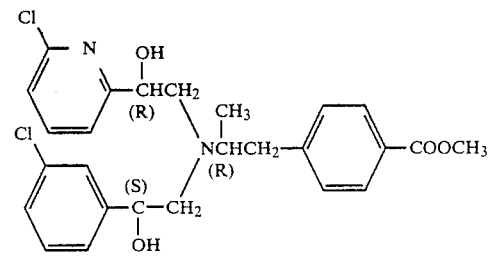

7. A compound according to claim 1, 2-[p-[(RS)-3-[[(RS)-2-(6-chloro-2-pyridyl)-2-hydroxyethyl]]p-(2-ethoxyethoxy)phenethyl]amino]-2-hydroxypropoxy]phenyl]acetamide, represented by the formula

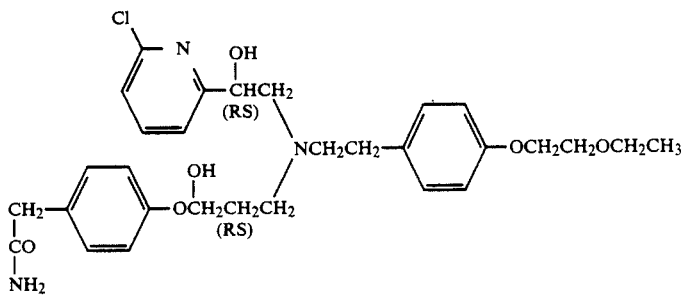

8. A compound according to claim 1, 4,'-[(RS)-3-[[(RS)-2-(6-chloro-2-pyridyl)-2-hydroethyl]][(R)-p-(2-ethoxyethoxy)-α-methylphenethyl]amino]-2-hydroxy-propoxy]acetanilide represented by the formula

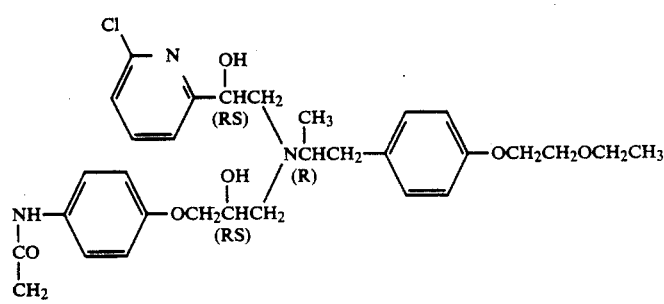

9. a compound according to claim 1 6-chloro-α-[[[(R)-p-(2-ethoxyethoxy)-α-methylphenethyl][(RS)-2-hydroxy-3-[p-[2-phenethoxy)ethoxy]phenoxy]propyl-]amino]methyl]-2-pyridinemethanol represented by the formula

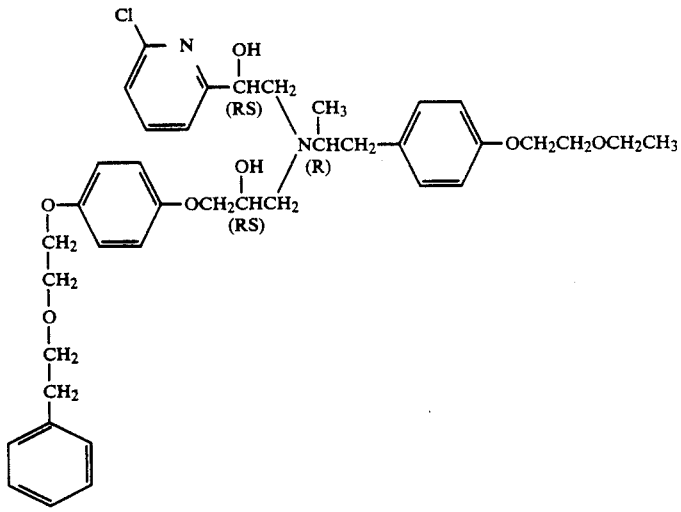

10. A pharmaceutical composition for treating conditions associated with an increased protein breakdown during convalescence after an operation comprising an effective amount of a compound of the formula

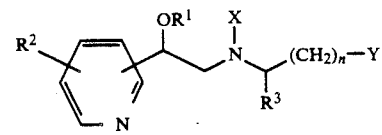

wherein
n is 1 or 2

X is a group $X^a$ of the formula

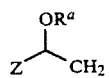

Z is a group of the formula

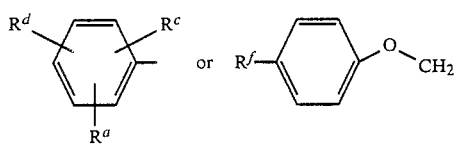 or 

Y is

R is $R^o$ or $OR''$ $R^o$ is lower-alkyl, $COR^4$ or $C(R^5)=CHCOR^4$, $R''$ is hydrogen, lower-alkyl, lower-alkanoyl, $(CH_2)_{1-6}$—OH, $(CH_2)_{1-6}$—$O(CH_2)_{1-6}$—$R^6$ or $(CH_2)_{1-6}$—$COR^4$ $R^1$ and $R^a$ are hydrogen, lower-alkanoyl, benzoyl or $(CH_2)_{1-6}$—OH $R^2$ is hydrogen, Cl, Br or $CF_3$, $R^3$ and $R^5$ are hydrogen or $CH_3$, $R^4$ is hydroxy, lower-alkoxy or $N(R^7,R^8)$, $R^6$ is hydrogen, $R^g$, OH or $COR^4$, $R^7$ and $R^8$ are hydrogen or lower-alkyl, $R^c$ and $R^e$ are hydrogen, Cl, F, Br or $CF_3$, $R^d$ is hydrogen or $NH_2$, $R^f$ is hydrogen, $CH_3CONH$, $NH_2COCH_2$ or $R^9CH_2CH_2OCH_2CH_2O$, $R^g$ and $R^9$ are phenyl or phenyl substituted by Cl, F or Br, an enantiomer, diastereomer or racemate thereof or a physiologically compatible salt thereof, and an inert carrier.

11. A pharmaceutical composition according to claim 10 wherein $R^4$ in the group Y is lower-alkoxy or $N(R^7, R^8)$.

12. A pharmaceutical composition according to claim 11, wherein n is the integer 1, $R^1$ is hydrogen, $R^2$ is chlorine in the 6-position of a 2-pyridyl residue and Y is phenyl substituted in the p-position by R.

13. A pharmaceutical composition according to claim 12, wherein X is $X^a$; $R^a$ is hydrogen; Z is phenoxymethyl substituted in the p-position by carbamoylmethyl, acetamide or 2-phenethoxyethoxy, and Y is p-(2-ethoxyethoxy)phenyl.

14. A compound according to claim 13, wherein $R^3$ is hydrogen or methyl with the R-configuration.

15. A method of treating conditions associated with an increased protein breakdown which comprises administering to a host requiring such treatment an effective amount of a compound

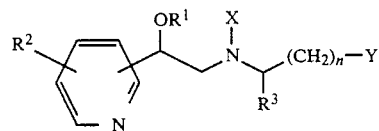

wherein
n is 1 or 2
X is a group $X^a$ of the formula

Z is a group of the formula

 or 

Y is

R is $R^0$ or $OR''$ $R^o$ is lower-alkyl, $COR^4$ or $C(R^5)=CHCOR^4$, $R''$ is hydrogen, lower-alkyl, lower-alkanoyl, $(CH_2)_{1-6}$—OH, $(CH_2)_{1-6}$—$O(CH_2)_{1-6}$—$R^6$ or $(CH_2)_{1-6}$—$COR^4$ $R^1$ and $R^a$ are hydrogen, lower-alkanoyl, benzoyl or $(CH_2)_{1-6}$—OH $R^2$ is hydrogen, Cl, Br or $CF_3$, $R^3$ and $R^5$ are hydrogen or $CH_3$, $R^4$ is hydroxy, lower-alkoxy or $N(R^7, R^8)$, $R^6$ is hydrogen, $R^g$, OH or $COR^4$, $R^7$ and $R^8$ are hydrogen or lower-alkyl, $R^c$ and $R^e$ are hydrogen, Cl, F, Br or $CF_3$, $R^d$ is hydrogen or $NH_2$, $R^f$ is hydrogen, $CH_3CONH$, $NH_2COCH_2$ or $R^9CH_2CH_2OCH_2CH_2O$, $R^g$ and $R^9$ are phenyl or phenyl substituted by Cl, F or Br, an anantiomer, diastereomer or racemate thereof or a physiologically compatible salt thereof.

16. A method according to claim 15, wherein $R^4$ in the group Y is lower-alkoxy or $N(R^7, R^8)$.

17. A method according to claim 16, wherein n is the integer 1, $R^1$ is hydrogen, $R^2$ is chlorine in the 6-position of a 2-pyridyl residue and Y is phenyl substituted in the p-position by R.

18. A method according to claim 17, wherein X is $X^a$; $R^a$ is hydrogen; Z is phenoxymethyl substituted in the p-position by carbamoylmethyl, acetamide or 2-phenethoxyethoxy, and Y is p-(2-ethoxyethoxy)phenyl.

19. A method according to claim 18, wherein $R^3$ is hydrogen or methyl with the R-configuration.

20. A feed composition for veterinary use in the maintenance of fattening animals which comprises an effective amount of a compound

wherein
n is 1 or 2
X is a group $X^a$ of the formula

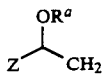

Z is a group of the formula

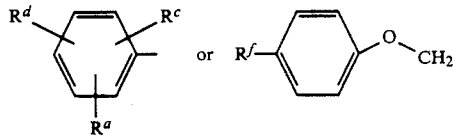

Y is

R is $R^o$ or $OR''$
$R^o$ is lower-alkyl, $COR^4$ or $C(R^5)=CHCOR^4$,
$R''$ is hydrogen, lower-alkyl, lower-alkanoyl, $(CH_2)_{1-6}$—OH, $(CH_2)_{1-6}$—O$(CH_2)_{1-6}$—$R^6$ or $(CH_2)_{1-}$—$OR^4$
$R^1$ and $R^a$ are hydrogen, lower-alkanoyl, benzoyl or $(CH_2)_{1-6}$—OH
$X^a$
Z
$R^2$ is hydrogen, Cl, Br or $CF_3$,
$R^3$ and $R^5$ are hydrogen or $CH_3$,
$R^4$ is hydroxy, lower-alkoxy or $N(R^7, R^8)$,
$R^6$ is hydrogen, $R^g$, OH or $COR^4$,
$R^7$ and $R^8$ are hydrogen or lower-alkyl,
$R^c$ and $R^e$ are hydrogen, Cl, F, Br or $CF_3$,
$R^d$ is hydrogen or $NH^2$,
$R^f$ is hydrogen, $CH_3CONH$, $NH_2COCH_2$ or $R^9CH_2CH_2OCH_2CH_2O$,
$R^g$ and $R^9$ are phenyl or phenyl substituted by Cl, F or Br,
an enantiomer, diastereomer or racemate thereof or a physiologically compatible salt thereof, and an inert carrier.

21. A feed composition according to claim 20, wherein $R^4$ in the group Y is lower-alkoxy or $N(R^7, R^8)$.

22. A feed composition according to claim 21, wherein n is the integer 1, $R^1$ is hydrogen, $R^2$ is chlorine in the 6-position of a 2-pyridyl residue and Y is phenyl substituted in the p-position by R.

23. A feed composition according to claim 20, wherein is $X^a$; $R^a$ is hydrogen; Z is phenoxymethyl substituted in the p-position by carbamoylmethyl, acetamide or 2-phenethoxyethoxy, and Y is p-(2-ethoxyethoxy)phenyl.

24. A feed composition according to claim 23, wherein $R^3$ is hydrogen or methyl with the R-configuration.

* * * * *